United States Patent [19]

Ashton et al.

[11] Patent Number: 4,568,539
[45] Date of Patent: Feb. 4, 1986

[54] BODY POWDER COMPOSITIONS

[75] Inventors: William H. Ashton, Philadelphia, Pa.; Robert S. Russell, South River; David C. Zajac, East Brunswick, both of N.J.

[73] Assignee: Johnson & Johnson Baby Products Company, New Brunswick, N.J.

[21] Appl. No.: 519,872

[22] Filed: Aug. 3, 1983

[51] Int. Cl.[4] ............................................. A61K 7/035
[52] U.S. Cl. ...................................... 424/69; 514/778
[58] Field of Search .................. 424/69, 361; 426/661, 426/578; 127/29, 32

[56] References Cited

U.S. PATENT DOCUMENTS

| | | | |
|---|---|---|---|
| 480,669 | 8/1892 | Norfolk | 127/32 X |
| 3,171,747 | 3/1965 | Kessinger | 426/661 X |
| 3,528,853 | 9/1970 | Pelton | 127/32 X |
| 3,836,680 | 9/1974 | Salza | 426/661 X |
| 4,192,900 | 3/1980 | Cheng | 127/32 X |
| 4,272,514 | 6/1981 | Spence | 424/69 |

OTHER PUBLICATIONS

Barnett, "Baby Powders", in Balsom et al., *Cosmetics: Science and Technology*, vol. I, pp. 152-154.

Primary Examiner—Esther M. Kepplinger
Assistant Examiner—Shawn P. Foley
Attorney, Agent, or Firm—Steven P. Berman

[57] ABSTRACT

Body powder compositions exhibiting excellent moisture absorbency comprising starch and a specific pregelatinized cornstarch.

8 Claims, No Drawings

BODY POWDER COMPOSITIONS

BACKGROUND OF THE INVENTION

The present invention relates to body powder compositions. More particularly, the present invention relates to starch body powder compositions with improved moisture absorbent properties.

Body powders have long been available to the consuming public primarily for absorbing moisture. Said moisture can, for example, be as a result of the secretion from the sebaceous and sweat glands. Body powders have also been used extensively on babies to help prevent diaper rash and to otherwise help maintain dryness.

High grade talcs have for many years been used in the form of powder for application to the skin. Talc, in its finely divided form, is well suited for this purpose. Thus, finely divided talc has found wide acceptance and application in the cosmetic industry and as a powder for treating tender skins, such as those of infants or children, to prevent chafing or other irritation as would occur from diapers or wet clothing.

Aside from talc, various other ingredients have also been proposed and utilized for body powders including starches, cellulose derivatives, polymeric substances and the like. Although many satisfactory talc and non-talc compositions are available through commercial channels, numerous attempts to develop improved compositions have been ongoing. Since one of the primary purposes of a body powder is to absorb moisture, the effectiveness of the body powder is diminished when the powder has reached its capacity for absorbence. Therefore, developments that increase the absorbency without decreasing the other desirable properties of powders are desired. Numerous compositions and additives have been suggested in the literature for this purpose and have met with varying degrees of success.

SUMMARY OF THE INVENTION

It is an object of this invention to provide improved body powder compositions.

It is another object of this invention to provide body powder compositions with improved moisture absorbency.

It is a still further object of this invention to provide starch body powder compositions with improved moisture absorbency.

Other objects of this invention will be set forth in, or be apparent from, the following detailed description of the invention.

The foregoing objects and other features and advantages of the present invention are achieved by a composition comprising a major amount of a conventional starch, preferably cornstarch, and a minor amount of a specific pregelatinized cornstarch.

DETAILED DESCRIPTION OF THE INVENTION

The present invention relates to body powder compositions consisting of from about 99 to 80% starch and from about 1 to 20% of a pregelatinized cornstarch and may also contain other components normally utilized in such compositions.

Powdered starches have been used for many years in dusting powder applications. While starches from various sources such as cornstarch, potato starch, sago starch, rice starch, tapioca starch, and the like are commercially available, the most readily available form of starch for the desired use is cornstarch. Cornstarch is preferred since it has demonstrated skin affinity, uniform natural globular particle dimensionality and purity as well as its ready availability. Most cornstarch normally produced for industrial, food and pharmaceutical uses is derived from field corn known commonly as yellow dent corn. This cornstarch consists of irregular, angular white granules or fine powder of chiefly spherical to polygonal shaped particles. The particle size is such that not less than 99% passes through a 100 mesh screen and preferably at least 98% will pass through a 200 mesh screen. This cornstarch is utilized in an amount of from about 99 to 80% by weight of the total composition, preferably from about 97.5 to 90% by weight of the total composition.

The pregelatinized cornstarch which is useful in the present invention is derived specifically from waxy maize corn. The pregelatinized cornstarch is cornstarch that has been chemically or mechanically processed to rupture all or part of the granules, preferably in the presence of water and subsequently dried. This pregelatinization of the cornstarch is achieved by well-known processing techniques in the starch industry. Generally, this process involves dispersing a cornstarch, preferably waxy maize cornstarch, into a dilute water slurry which is then doctored onto a drum drier internally heated by superheated steam. The surface temperature of the drum boils the slurry and simultaneously converts it to a pregelatinized form and also dries the boiled starch mixture into a film which is then stripped from the drum by a scraper blade. It has now been found that subsequently milling or grinding this film forms flaky particles of particle size such that at least 80%, and preferably about 98%, passes through a 200 mesh screen. These particles should have a bulk density of from about 3.0 gm./cubic in. to about 7.0 gm./cubic in. and a moisture content no greater than about 14% by weight and preferably no greater than about 7% by weight, to be suitable for use in the compositions of the present invention.

The specific pregelatinized cornstarch is utilized in from about 1.0 to 20% by weight of the total composition, preferably from about 2.5 to 10%. If less than about 1.0% by weight of the total composition is utilized then the desired advantages will not be readily achieved. If greater than about 20% by weight of the total composition is utilized then tactile properties such as texture, smoothness and lubricity could be adversely affected.

Other components normally found in body powder compositions can be added, if desired. Such components include flow agents such as tricalcium phosphate, dyes and colorings, bactericides, medicaments and perfumes.

The perfumes which are useful in the present invention include any commercial perfume which results in the fragrance desired by the formulator of the powder compositions. Commercial perfumes are mixture of many components and these components all contribute to the particular fragrance which is characteristic of the mixture. In obtaining the desired fragrance, the ratio of components might be changed, some components may be added and some omitted.

Examples of typical perfume components which can be formulated to make up a particular pleasant aroma when used in a body powder product include: lemon oil, musk ketone, ionone, diphenyl oxide, cedarwoodterpeneless, geranyl acetate, ylang ylang oil; cedryl acetate, isoeugenol, cinnamic alcohol, aurantheol, methyl anthranilate, vanillin, oil bergamot, eugenol, oil of cananga, citral, tetrahydro linalool, oil patchouly, methyl isoeugenol, hexylcinnamic aldehyde, resil oilbanum, resin balsam fir, musk aurbrette, resin balsam Peru, oil sandalwood, geraniol, terpenyl acetate, benzyl isoeugenol, oil copaiba, oil nutmeg, rhodinol, diphenyl methane, hydroxycitronellal, methyl benzoate, benzyl propionate, oil palmarose, oil orange, oil geranium, methyl gamma ionone, oil of lavender and the like.

The perfume is utilized in an amount of from about 0.01 to 1.0% by weight of the total composition, preferably from about 0.1 to 0.5% by weight of the total composition. If greater than about 1.0% by weight of perfume is utilized, the fragrance will usually be too strong initially and may deteriorate quickly; and if less than 0.01% by weight of perfume is utilized, the fragrance will not be discernible to the user of the product.

The compositions of the present invention can be prepared by well-known mixing or blending procedures. For example, the cornstarch and pregelatinized cornstarch and other ingredients, if utilized, are mixed and thoroughly blended and the perfume is then uniformly mixed therein. The resulting powder compositions exhibit excellent moisture absorbency.

Specific embodiments of the powder compositions prepared in accordance with the present invention are illustrated by the following representative examples. It will be understood, however, that the invention is not confined to the specific limitations set forth in the individual examples, but rather to the scope of the appended claims.

EXAMPLE I

A body powder composition is prepared as follows: 95.65 parts of conventional cornstarch, 2.5 parts of pregelatinized cornstarch and 1.5 parts of tricalcium phosphate are placed in a PK Blender manufactured by Patterson-Kelley, East Stroudsburg, Pa., with a liquid addition bar and the Blender is activated. 0.35 parts of fragrance are then added through the liquid addition bar and mixing is continued for five minutes, followed by tumbling for 15 minutes.

The resulting powder composition has the following formulation:

|  | % w/w |
| --- | --- |
| cornstarch | 95.65 |
| pregelatinized cornstarch | 2.50 |
| tricalcium phosphate | 1.50 |
| fragrance | 0.35 |
|  | 100.00 |

EXAMPLE II

In order to demonstrate that the body powder compositions prepared in accordance with the present invention exhibit excellent moisture absorbency, the following experiment is performed.

A body powder composition is prepared in accordance with the procedure of Example I and is designated Composition A. Two additional body powder compositions, i.e., Compositions B and C are prepared by the same procedure and contain 5.00% and 8.00% w/w, respectively, of the pregelatinized cornstarch. A further composition is prepared as a control containing no pregelatinized cornstarch and is designated Composition D.

These body powder compositions are then tested in accordance with the following gravimetric absorbency test procedure:

Approximately 2.0 gms of each powder composition is uniformly dispersed over the surface of a glass fiber filter disc. A circular layer of powder 5½ cm in diameter is obtained giving a powdered area of 24 sq. cm. and approximately 1½ mm thick. The powdered disc is then placed on a porous glass plate connected by a continuous liquid bridge to a reservoir of 1% saline solution located at 5 mm below the plate so a slight negative head pressure exists at the liquid/powder interface. This slight negative head pressure assures that liquid taken up by the powder is due to its "demand absorbency" wicking potential and not to a positive head pressure force. The amount of solution absorbed by the powder is electronically detected and recorded to an accuracy of 0.01 gms. Absorbency is stated in terms of cc of saline absorbed per gram of powder. The absorbent capacity in this thin layer test is determined by the fluid uptake in 5 minutes. This test procedure and the apparatus utilized therein is more fully set forth in U.S. Pat. No. 4,357,827 which is incorporated herein by reference. The results of the test are shown in Table I below wherein the absorbency of Compositions A, B and C are compared to Composition D and the results shown as % Absorbency Increase over the control, i.e., Composition D:

TABLE I

| Composition | % Pregelatinized Cornstarch | Absorbency cc/gm. | % Absorbency Increase |
| --- | --- | --- | --- |
| A | 2.5 | 1.17 | 37.6 |
| B | 5.0 | 1.39 | 63.5 |
| C | 8.0 | 1.68 | 91.8 |
| D | 0 | 0.85 | — |

The above results clearly demonstrate that the compositions of the present invention containing the pregelatinized cornstarch exhibit significant increased absorbency when compared to the same composition without the pregelatinized cornstarch. These compositions also exhibit good flowability and tactile properties.

EXAMPLES III-X

Body powder compositions containing 1%, 5%, 10%, 15%, 20% 25% and 30% pregelatinized cornstarch were prepared in accordance with the procedure of Example I as well as a control composition containing no pregelatinized cornstarch. These compositions have the following formulations:

| Example | % Cornstarch | % Pregelatinized Cornstarch | % Tricalcium Phosphate | % Fragrance |
| --- | --- | --- | --- | --- |
| III | 97.15 | 1.0 | 1.5 | 0.35 |
| IV | 93.15 | 5.0 | 1.5 | 0.35 |
| V | 88.15 | 10.0 | 1.5 | 0.35 |
| VI | 83.15 | 15.0 | 1.5 | 0.35 |
| VII | 78.15 | 20.0 | 1.5 | 0.35 |
| VIII | 73.15 | 25.0 | 1.5 | 0.35 |
| IX | 68.15 | 30.0 | 1.5 | 0.35 |
| X | 98.15 | 0 | 1.5 | 0.35 |

EXAMPLE XI

The compositions of Examples III–X are tested in accordance with the test procedure set forth in Example II and the results are as follows:

| Composition | % Pregelatinized Cornstarch | Absorbency cc/g | % Absorbency Increase |
| --- | --- | --- | --- |
| Example III | 1.0 | 0.99 | 11.2 |
| Example IV | 5.0 | 1.36 | 52.8 |
| Example V | 10.0 | 1.82 | 104.5 |
| Example VI | 15.0 | 2.03 | 128.1 |
| Example VII | 20.0 | 1.87 | 110.1 |
| Example VIII | 25.0 | 1.45 | 62.9 |
| Example IX | 30.0 | 1.33 | 49.4 |
| Example X | 0 | 0.89 | — |

The above results clearly demonstrate that the compositions of the present invention containing the pregelatinized cornstarch exhibit significant increased absorbency when compared to the same composition without the pregelatinized cornstarch. The compositions containing from 1 to 20% pregelatinized cornstarch also exhibit good flowability characteristics and tactile properties whereas the compositions containing 25% and 30% pregelatinized cornstarch do not exhibit satisfactory flowability characteristics and tactile properties.

Various other features and embodiments of the present invention not specifically enumerated will be obvious to those skilled in the art, all of which may be achieved without departing from the spirit and the scope of the invention as defined by the following claims.

We claim:

1. A body powder composition consisting essentially of a powder of from about 99 to 80% by weight of the total composition starch and from about 1 to 20% by weight of the total composition pregelatinized cornstarch.

2. The composition of claim 1 wherein the starch is selected from the group consisting of cornstarch, potato starch, sago starch, rice starch and tapioca starch.

3. The composition of claim 2 wherein the starch is cornstarch.

4. The composition of claim 1 wherein the pregelatinized cornstarch is present from about 2.5 to 10% by weight of the total composition.

5. A body composition consisting essentially of a powder of from about 1 to 20% by weight of the total composition pregelatinized cornstarch, from about 0.01 to 1.00% by weight of the total composition perfume and the balance starch.

6. The composition of claim 5 wherein the starch is selected from the group consisting of cornstarch, potato starch, sago starch, rice starch and tapioca starch.

7. The composition of claim 6 wherein the starch is cornstarch.

8. The composition of claim 5 wherein the pregelatinized cornstarch is present from about 2.5 to 10% by weight of the total composition.

* * * * *